(12) United States Patent
Jones et al.

(10) Patent No.: US 10,383,798 B2
(45) Date of Patent: Aug. 20, 2019

(54) BENEFIT DELIVERY PARTICLE COMPRISING A PHENYLALANINE CHITOSAN SALT

(71) Applicant: Conopco, Inc., Englewood Cliffs, NJ (US)

(72) Inventors: Christopher Clarkson Jones, Wirral (GB); Kenneth Stuart Lee, Wirral (GB); Xiaoyun Pan, Shanghai (CN); Yan Wu, Shanghai (CN); Yuanyuan Zhang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 91 days.

(21) Appl. No.: 15/572,359

(22) PCT Filed: May 9, 2016

(86) PCT No.: PCT/EP2016/060311
§ 371 (c)(1),
(2) Date: Nov. 7, 2017

(87) PCT Pub. No.: WO2016/180769
PCT Pub. Date: Nov. 17, 2016

(65) Prior Publication Data
US 2018/0116918 A1    May 3, 2018

(30) Foreign Application Priority Data

May 13, 2015  (WO) ................. PCT/CN2015/078846
Jul. 9, 2015  (EP) ..................................... 15176072

(51) Int. Cl.
| | |
|---|---|
| C11D 3/50 | (2006.01) |
| A61K 8/11 | (2006.01) |
| A61Q 5/00 | (2006.01) |
| A61Q 5/02 | (2006.01) |
| A61K 8/73 | (2006.01) |
| A61K 8/02 | (2006.01) |
| A61K 8/44 | (2006.01) |
| A61K 8/49 | (2006.01) |
| A61K 8/60 | (2006.01) |
| B01J 13/14 | (2006.01) |
| B01J 13/22 | (2006.01) |

(52) U.S. Cl.
CPC .................. *A61K 8/11* (2013.01); *A61K 8/02* (2013.01); *A61K 8/44* (2013.01); *A61K 8/445* (2013.01); *A61K 8/4913* (2013.01); *A61K 8/4946* (2013.01); *A61K 8/60* (2013.01); *A61K 8/73* (2013.01); *A61Q 5/00* (2013.01); *A61Q 5/02* (2013.01); *B01J 13/14* (2013.01); *B01J 13/22* (2013.01); *A61K 2800/56* (2013.01); *A61K 2800/624* (2013.01); *A61K 2800/80* (2013.01); *C11D 3/505* (2013.01)

(58) Field of Classification Search
CPC ...................................................... C11D 3/505
See application file for complete search history.

(56) References Cited

U.S. PATENT DOCUMENTS

| | | | |
|---|---|---|---|
| 8,795,643 B1 * | 8/2014 | Anthony | .................. A61Q 5/06 424/70.11 |
| 9,078,818 B1 * | 7/2015 | Anthony | .............. A61K 8/0233 |
| 2010/0173002 A1 * | 7/2010 | Yulai | ...................... A23L 33/19 424/492 |

FOREIGN PATENT DOCUMENTS

| | | |
|---|---|---|
| EP | 1547625 | 6/2005 |
| WO | WO2008017962 | 2/2008 |
| WO | WO2009020314 | 2/2009 |
| WO | WO2014064121 | 5/2014 |

OTHER PUBLICATIONS

IPRP2 in PCTEP2016060311, dated Jun. 12, 2017.
Search Report and Written Opinion in EP15176072, dated Dec. 16, 2015.
Search Report and Written Opinion in PCTEP2016060311, dated Jun. 24, 2016.
Written Opinion in PCTEP2016060311, dated Mar. 27, 2017.

* cited by examiner

*Primary Examiner* — Charles I Boyer
(74) *Attorney, Agent, or Firm* — Greenberg Traurig, LLP

(57) ABSTRACT

Disclosed is a benefit agent delivery particle comprising a benefit agent; and a chitosan salt at the outer surface of the particle, wherein the chitosan salt comprises a chitosan component and amino acid anion, wherein the amino acid comprises phenylalamine; the amino acid does not comprises tyrosine; and the amino acid does not comprises histidine or the amino acid comprises no greater than 20% of histidine by mole of the total amino acid, wherein the benefit agent comprises fragrance, pro-fragrance, hair conditioning agent, anti-dandruff agent, moisturizers, emollients, dyes, pigments, color care additives, or a mixture thereof.

11 Claims, No Drawings

BENEFIT DELIVERY PARTICLE COMPRISING A PHENYLALANINE CHITOSAN SALT

FIELD OF THE INVENTION

The present invention relates to benefit delivery particles which have higher deposition efficiency on tip hair. Moreover, the present invention also relates to composition comprising the particles and process for the production of the particles.

BACKGROUND OF THE INVENTION

Many home care and personal care products seek to deliver benefit agents to substrates such as textiles, hard surfaces, hair and skin. To achieve a long-lasting benefit agent release performance, encapsulation of the benefit agent in particles has been proposed as a means, in particular for the perfume.

However, for some special product, in particular hair treatment product, some benefit agent need to be delivered onto specific position. For example, it is desirable to deliver more conditioning silicone onto tip and/or middle of the hair to have a better conditioning effect and/or to avoid unpleasant greasy and unclean sensory.

Thus, we have recognized a need to develop new encapsulation particles which is capable of being deposited onto tip hair with higher deposition when included into a hair treatment composition. We therefore developed a benefit agent delivery particle comprising a benefit agent; and a chitosan salt at the outer surface of the particle, wherein the chitosan salt comprises a chitosan component and amino acid anion, wherein the amino acid comprises phenylalanine; the amino acid does not comprises tyrosine; and the amino acid does not comprises histidine or the amino acid comprises no greater than 20% of histidine by mole of the total amino acid, wherein the benefit agent comprises fragrance, pro-fragrance, hair conditioning agent, anti-dandruff agent, moisturizers, emollients, dyes, pigments, colour care additives, or a mixture thereof. It was surprisingly found that when included into a shampoo, the particles have better deposition on tip hair.

SUMMARY OF THE INVENTION

In a first aspect, the present invention is directed to a benefit agent delivery particle comprising a benefit agent; and a chitosan salt at the outer surface of the particle, wherein the chitosan salt comprises a chitosan component and amino acid anion, wherein the amino acid comprises phenylalanine; the amino acid does not comprises tyrosine; and the amino acid does not comprises histidine or when the amino acid comprises histidine, the amino acid comprises no greater than 20% of histidine by mole of the total amino acid, wherein the benefit agent comprises fragrance, pro-fragrance, hair conditioning agent, anti-dandruff agent, moisturizers, emollients, dyes, pigments, colour care additives, or a mixture thereof.

In a second aspect, the present invention is directed to a composition comprising a particle of the present invention, and at least one surfactant.

In a third aspect, the present invention is directed to a process for the production of particle of the present invention, the process comprising a) encapsulating a core using emulsion polymerization to form a particle, and b) attaching chitosan salt onto the outer surface of the particle, wherein the benefit agent is either present in or as the core during step (a) of the process or adsorbed into the core in a subsequent step.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Particle size" as used herein refers to particle diameter unless otherwise stated. For samples having particulate with diameter no greater than 1 μm, diameter means the z-average particle size measured, for example, using dynamic light scattering (see international standard ISO 13321) with an instrument such as a Zetasizer Nano™ (Malvern Instruments Ltd, UK). For samples having particulate with diameter greater than 1 μm, diameter means the apparent volume median diameter (D50, also known as ×50 or sometimes d(0.5)) of the particles measurable for example, by laser diffraction using a system (such as a Mastersizer™ 2000 available from Malvern Instruments Ltd) meeting the requirements set out in ISO 13320.

"Water insoluble" as used herein refers to that the solubility in water is less than 1 gram per 100 gram of water, preferably less than 1 gram per 1 kilogram of water, at 25° C. and at atmospheric pressure.

One benefit of small particles is that they are less visible in clear products. However, if the particles are too small then it can become difficult to break thereby releasing the benefit agent. Therefore the particle preferably has an average particle size of 0.1 to 50 μm, more preferably from 0.3 to 40 μm, even more preferably from 0.5 to 20 μm, still even more preferably from 1 to 10 μm and most preferably from 1.4 to 6 μm.

To have a better deposition on hair, the zeta potential of the particles as measured using a Malvern Nano ZS90 apparatus, in DI water at a solid content of 50 ppm and pH of 7 at 25° C., is preferably at least 5 mV, more preferably at least 15 mV, even more preferably at least 20 mV.

Benefit agents according to the present invention refers to agents which may provide a range of benefits to hair and/or scalp, and more preferably to human hair. The benefit agent is typically present in an amount of from 10 to 90% by total weight of the particle, more preferably from 30 to 80% by total weight of the particle.

Various benefit agents can be incorporated into the particles. Where the end use of the particles is in connection with the preferred surfactant-containing formulations, any compatible benefit agent which can provide a benefit to a substrate which is treated with a preferable surfactant-containing composition can be used. Advantages of the particles of the invention are a good deposition onto tip hair, even in the presence of surfactant.

The benefit agents include fragrance, pro-fragrance, hair conditioning agent, anti-dandruff agent, moisturizers, emollients, dyes and/or pigments, colour care additives (including dye fixing agents), or a mixture thereof. Preferably, the benefit agent comprises fragrance, pro-fragrance, hair conditioning agent or a mixture thereof. More preferably, the benefit agent is fragrance and/or pro-fragrance, and most preferably the benefit agent is fragrance.

Useful components of the fragrance include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Fragrance and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally fragranced or flavoured, or of modifying the odour and/or taste of said consumer product.

By fragrance in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a fragrance composition and in those embodiments of the invention which contain an increased level of top-notes it is envisaged at that least 20% wt would be present within the particle.

Another group of fragrances with which the present invention can be applied are the so-called 'aromatherapy' materials. These include many components also used in fragrancery, including components of essential oils such as Clary Sage, Eucalyptus, Geranium, Lavender, Mace Extract, Neroli, Nutmeg, Spearmint, Sweet Violet Leaf and Valerian.

Typical fragrance components which it is advantageous to employ in the embodiments of the present invention include those with a relatively low boiling point, preferably those with a boiling point of less than 300, preferably 100-250 Celsius, measured at one atmosphere.

It is also advantageous to encapsulate fragrance components which have a low Log P (i.e. those which will be partitioned into water), preferably with a Log P of less than 3.0.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols.

The fragrance is typically present in an amount of from 10-85% by total weight of the particle, preferably from 15 to 75% by total weight of the particle. The fragrance suitably has a molecular weight of from 50 to 500 Dalton. Pro-fragrances can be of higher molecular weight, being typically 1-10 kD.

Hair conditioning agent may be selected from silicone conditioning agent, cationic surfactant, cationic deposition polymer, non-silicone oily material or a combination thereof. More preferably the hair condition agent comprises silicone conditioning agent, cationic deposition polymer or mixture thereof and most preferably the hair conditioning agent is silicone conditioning agent.

Suitable silicone conditioning agents include polydiorganosiloxanes, in particular polydimethylsiloxanes which have the CTFA designation dimethicone. Also suitable are polydimethyl siloxanes having hydroxyl end groups, which have the CTFA designation dimethiconol. Also suitable are silicone gums as described for example in WO 96/31188. These materials can impart body, volume and stylability to hair, as well as good wet and dry conditioning. Also suitable are functionalised silicones, particularly amino-functionalised silicones.

Suitable non-silicone oily conditioning agents are selected from hydrocarbon oils, fatty esters and mixtures thereof.

The chitosan salt suitable for the present invention comprises a chitosan component and amino acid anion. Preferably the chitosan component of the salt (as a protonated material) has a viscosity average molecular weight of at least 10,000 Daltons, more preferably in the range of from 30,000 to 1000,000 Daltons, even more preferably from 70,000 to 600,000 Daltons, and still even more preferably from 150,000 to 400,000 Daltons. Preferably, the deacetylation degree of the chitosan component is at least 65%, more preferably from 70 to 95%, even more preferably from 72 to 90% and most preferably from 75 to 85%.

Preferably, the chitosan component comprises at least 5%, more preferably at least 10% of protonated primary amino group, by mole of the total amount of primary amino group and protonated primary amino group.

The chitosan salt comprises a chitosan component and amino acid anion. Preferably the amino acid comprises glutamine, glutamic acid, histidine, leucine, lysine, serine, threonine, or a mixture thereof. More preferably the amino acid comprises histidine, lysine or a mixture thereof. Even more preferably the amino acid comprises lysine and phenylalanine. Most preferably, the amino acid comprises phenylalanine, lysine and glutamic acid. Preferably, the amino acid comprises phenylalanine in amount of at least 20%, more preferably at least 29% by mole of the total amino acid. It shall be noted that when the chitosan salt comprises more than one amino acid anion, it typically refers that the chitosan salt contains more than one amino acid anion instead of mixture of chitosan salts which contains single amino acid anion.

Typically the particle comprises water insoluble non-polysaccharide polymer, water insoluble inorganic salt or a mixture thereof, more preferably the particle comprises water insoluble non-polysaccharide polymer. Inorganic salt may be selected from clay, zeolite, silica, amorphous silicate, crystalline nonlayer silicate, layer silicate, calcium carbonate, sodium carbonate, sodalite, and alkali metal phosphates.

Preferably, the water insoluble non-polysaccharide polymer comprises polyvinyl pyrrolidone, polyvinyl alcohol, cellulose ether, polystyrene, polyacrylate, polymethacrylate, polyolefin, aminoplast polymer, polyacrylamide, acrylate-acrylamide copolymer, melamine-formaldehyde condensate, urea-formaldehyde condensate, polyurethane, polysiloxane, polyurea, polyamide, polyimide, polyanhydride, polyolefin, polysulfone, polysaccaharide, polylactide, polyglycolide, polyorthoester, polyphosphazene, silicone, lipid, polyester, ethylene maleic anyhydride copolymer, styrene maleic anyhydride copolymer, ethylene vinyl acetate copolymer, lactide glycolide copolymer, or combinations of these materials. More preferably, the inner shell comprises polystyrene, polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccaharide or a mixture thereof. More preferably, the water insoluble non-polysaccharide polymer comprises polystyrene, modified polyvinyl alcohol, polyacrylate, polymethacrylate, polyolefin, aminoplast polymers, melamine-formaldehyde condensate, urea-formaldehyde condensate, polyurethane or a mixture thereof. Even more preferably the water insoluble non-polysaccharide polymer comprises polystyrene, modified polyvinyl alcohol, polyolefin, polyurethane or a mixture thereof. Still even more preferably, the water insoluble non-polysaccharide polymer comprises polystyrene, modified polyvinyl alcohol or a combination thereof and most preferably, the water insoluble non-polysaccharide polymer is polystyrene, modified polyvinyl alcohol, or a combination thereof.

Typically, the particles comprise an inner region, forming a "core" which comprises the benefit agent, an "inner shell" which comprises the water insoluble non-polysaccharide polymer, water insoluble inorganic salt or a mixture thereof, and an "outer shell" which comprises the chitosan salt at the outer surface of the particle. The core may comprise a droplet of the benefit agent or may comprise a polymer matrix into which the benefit agent is adsorbed. More preferably, the particle comprises a core comprising the benefit agent, an inner shell comprising the water insoluble non-polysaccharide polymer, and an outer shell comprising the chitosan salt at the outer surface of the particle.

Preferably, the core comprises at least 5% of fragrance by weight of the core, more preferably from 10% to 100% by weight of the core, even more preferably from 35% to 100% by weight of the core.

For sake of clarity, it should be noted that the outer shell is different from the inner shell. Preferably at least 20% of the outer shell by weight, more preferably at least 50% of the outer shell by weight, even more preferably at least 80% by weight of the outer shell is chitosan salt. Most preferably, the outer shell is the chitosan salt.

Preferably, the chitosan salt is bound to the particle by means of a covalent bond, entanglement or strong adsorption, more preferably by a covalent bond or entanglement, and most preferably by means of a covalent bond. It is important that the chitosan salt is not removed by water from the particle as it cannot then function effectively as a delivery aid. Thus, for example spray-drier coating of chitosan onto particles would not result in chitosan being an effective delivery aid as the chitosan would be removed from the particles on exposure to water. "Entanglement" as used herein refers to that the chitosan salt is adsorbed onto the particle as the polymerization proceeds and the particle grows in size. It is believed that under such circumstances part of the adsorbed chitosan salt becomes buried within the interior of the particle. Hence at the end of the polymerization, part of the chitosan salt is entrapped and bound in the polymer matrix of the particle, whilst the remainder is free to extend into the aqueous phase.

The particle of the present invention may be manufactured by any process, however, it is preferred that the process for producing the benefit agent delivery particle comprises the step of:

a) encapsulating a core using emulsion polymerization to form a particle, and
b) attaching chitosan salt onto the outer surface of the particle, wherein the benefit agent is either present in or as the core during step (a) of the process or adsorbed into the core in a subsequent step.

Preferably, the chitosan salt is attached onto the particle by means of a chemical linkage after the particle is essentially fully formed.

The present invention also provides a hair treatment composition. The end-product composition of the invention may be in any physical form but preferably a gel or liquid. The composition is more preferably an aqueous-based liquid.

The particle is typically included in the composition at levels of from 0.001% to 10%, preferably from 0.005% to 7.55%, most preferably from 0.01% to 5% by weight of the total composition.

Depending on the end-use compositions according to the present invention will typically contain one or more of surfactants (which may be anionic, cationic, non-ionic, zwitterionic and amphoteric), silicone conditioning agents and non-silicone oily conditioning agents, suspending agents, anti-dandruff agents, thickeners, cationic deposition polymers and shading agents. More preferably the composition comprises particle of the present invention and at least one surfactant.

Preferred anionic surfactants are the alkyl sulfates and alkyl ether sulfates. These materials have the respective formulae $R_2OSO_3M$ and $R_1O(C_2H_4O)_xSO_3M$, wherein $R_2$ is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Most preferably $R_2$ has 12 to 14 carbon atoms, in a linear rather than branched chain. The total amount of anionic cleansing surfactant in hair treatment compositions of the invention generally ranges from 0.5 to 45 wt %, more preferably from 1.5 to 20 wt %.

Preferably the surfactant comprises at least 3 wt % on total composition of an alkyl ether sulphate, in for example, a shampoo. When the composition is a conditioner a cationic surfactant is preferably included such as an alkyl ammonium material.

Hair treatment compositions according to the invention such as shampoos and conditioners suitably contain conditioning agents such as silicone conditioning agents and non-silicone oily conditioning agents.

Suitable silicone conditioning agents include polydiorganosiloxanes, in particular polydimethylsiloxanes which have the CTFA designation dimethicone. Also suitable for use in compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning. Also suitable are functionalised silicones, particularly amino-functionalised silicones.

The silicone conditioning agent is suitably present in hair treatment compositions at a level of from 0.05 to 10, preferably from 0.2 to 5, more preferably from 0.5 to 3 percent based on total weight of the composition.

Suitable non-silicone oily conditioning agents are preferably selected from hydrocarbon oils, fatty esters and mixtures thereof.

It is preferred that the hair treatment composition comprises a cationic deposition polymer, which may assist in deposition of ingredients in the composition. Preferably, the cationic deposition polymer is (or comprises) cationic polygalactomannan, especially guar or cassia derived polygalactomannan modified with hydroxypropyl trimonium chloride.

It is highly preferred that compositions according to the invention should contain from 0.01% to 2% wt. of the composition cationic deposition polymer, more preferably from 0.05 to 0.5% wt. and most preferably from 0.08 to 0.25% by weight of the composition.

Antidandruff agents are compounds that are active against dandruff and are typically antimicrobial agents and preferably antifungal agents.

Antifungal agents typically display a minimum inhibitory concentration of about 50 mg/ml or less against *Malassezia* spp.

Suitable antidandruff agents include compounds selected from azole based antifungal agents, octopirox, selenium sulfide, metal pyrithione salts, and mixtures thereof. The preferred azole based antifungal agents are ketoconazole and climbazole. Preferred metal pyrithione salts are zinc, copper, silver and zirconium pyrithione. The most preferred is zinc pyrithione.

Preferably, the antidandruff agent is present at from 0.01 to 5% wt. of the composition, more preferably from 0.1 to 2.5% wt. of the composition.

Suspending agent, if included, will preferably be present in a composition of the invention at levels of from 0.1 to 10%, more preferably from 0.5 to 6%, even more preferably from 0.9 to 4% by total weight of suspending agent based on the total weight of the composition.

The composition of the invention may contain other ingredients for enhancing performance and/or consumer acceptability. Such ingredients include dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

The composition preferably comprises at least 30% of water by weight of the composition, more preferably from 35 to 95%, even more preferably from 45 to 88%, still even more preferably from 55 to 82%, most preferably from 65 to 80% by weight of the total composition.

The present invention also provides a method of treating a substrate, the method comprising a step of treating the substrate with a composition comprising the particle of the present invention. Preferably the substrate is hair and/or scalp.

The invention will now be described with reference to the following non-limiting examples.

EXAMPLES

Materials

| Material | Supplier | Description |
|---|---|---|
| Polystyrene (PS) latex | Polysciences | Fluoresbrite yellow green (YG) microspheres (1 μm, 2.5% of solid content) |
| Chitosan | Aldrich | cat. # 448877, deacetylation degree: 75-85% |
| 1-Ethyl-3-(3-dimethylaminopropyl) carbodiimide hydrogen chloride (EDAC) | Alfa Aesar | — |
| Ethyl acetate (EtAc) | Sinopharm Chemical | AR grade |
| Acetic Acid | Sinopharm Chemical | AR grade |
| Sodium chloride | Sinopharm Chemical | AR grade |

Example 1

This example demonstrates the preparation of chitosan salt.

TABLE 1 component of amino acid mixture

| | Amino acids mixture (mol %) | | |
|---|---|---|---|
| | P1 | P5 | BMS |
| Glutamic acid | 20 | 11.5 | — |
| Histidine | — | 8 | — |
| Leucine | — | — | 14 |
| Lysine | 40 | — | — |
| Phenylalanine | 30 | 28.7 | 14 |
| Proline | — | 11.5 | 29 |
| Serine | 10 | 40.2 | 14 |
| Threonine | — | — | 14 |
| Glutamine | — | — | 14 |

The chitosan-amino acid salt was prepared using single amino acid or amino acid mixture in Table 1. Taking amino acid mixture P1 as an example, the typical procedure for preparation of chitosan salt is described as follows. 200 mg of chitosan was added into 20 ml of 0.5% acetic acid aqueous solution to form a mixture and the mixture was stirred until the chitosan was dissolved completely. The solution was denoted by chitosan-Ac solution. 1.48 g of amino acid mixture P1 (The total molar amount of amino acids was calculated to equal to the molar amount of the —$NH_2$ group of chitosan) was added to the chitosan-Ac solution. The mixture solution was then stirred for 24 hours until dissolved completely. The resultant aqueous product was denoted as chitosan-P1. Other chitosan-amino acid salts and chitosan-amino acid mixture salts in Table 2 were prepared by similar process.

TABLE 2 chitosan salt with different acids or acid mixtures

| Chitosan salt | Complexing acid | molar ratio of complexing acid to —$NH_2$ group of chitosan |
|---|---|---|
| Chitosan-P1 | P1 | 100% |
| Chitosan-P5 | P5 | 100% |
| Chitosan-BMS | BMS | 100% |
| Chitosan-Phe | Phenylalanine | 100% |
| Chitosan-Ser | Serine | 100% |

TABLE 2-continued chitosan salt with different acids or acid mixtures

| Chitosan salt | Complexing acid | molar ratio of complexing acid to —NH$_2$ group of chitosan |
|---|---|---|
| Chitosan-Pro | Proline | 100% |
| Chitosan-Arg | Arginine | 100% |

Example 2

This example demonstrates the surface attachment of chitosan salt onto latex particles via EDAC Coupling.

2a) Purification of PS Latex

The PS latex was purified by centrifugation, washed by DI water for three times and then dispersed in DI water to form dispersion with solid level of 5 wt %.

2b) Latex Particles Activation Using EDAC 40 mg of EDAC in 0.5 ml of DI water was added dropwise into the 5 ml of latex dispersion (solid content of 5 wt %) and then was stirred at room temperature for 3 hours. The latex dispersion was centrifuged to obtain the PS latex particles. Then the PS latex particles were washed by 1.0 ml of buffer (pH 7.0) twice followed by centrifugation each time. Then the PS latex particles were washed by 1.0 ml of DI water twice followed by centrifugation each time. The obtained pellet was re-dispersed in 1.0 ml of DI water with solid content of 2.5 wt %.

2c) Grafting of Chitosan Complex Onto Activated Latex Particles

Typically, 100 μl of the EDAC-activated PS latex was mixed with 150 μl of chitosan complex solution (Weight ratio of chitosan salt to PS latex particle: 0.6:1), and 600 μl of DI water was further added. The mixture was then agitated at 40° C. for 24 hours. After that, the modified PS latex was centrifuged followed by washing by DI water twice. The modified particle was dispersed to form dispersion with solid content of 0.5 wt %. The modified particle was denoted as PS-graff-Chitosan salt. A comparative sample (PS) without graft of any chitosan complex was prepared with PS latex solid content of 0.5 wt %.

TABLE 3

Sizes and Zeta Potentials of PS and modified PS particles

| Code of latex particles | Size (micron) | Zeta potential (mV) |
|---|---|---|
| PS | 1.1 | −39 |
| PS-graft-Chitosan-P1 | 1.7 | 40 |
| PS-graft-Chitosan-P5 | 1.5 | 25 |
| PS-graft-Chitosan-BMS | 1.7 | 26 |
| PS-graft-Chitosan-Phe | 1.6 | 20 |
| PS-graft-Chitosan-Ser | 1.6 | 7 |
| PS-graft-Chitosan-Pro | 2.1 | 23 |
| PS-graft-Chitosan-Arg | — | 44 |

2d) Characterization of Chitosan Salt Modified PS Latex Particle

The sizes and zeta potentials of the modified PS particles were measured by zeta potential analyzer (Zetasizer Nano ZS90, Malvern, USA) at 25° C. The particles were dispersed in water with solid content of 50 ppm and the pH of the dispersion was adjusted to about 7 for measurement. Each test was repeated three times. The average results of sizes and zeta potentials were listed in Table 3.

Example 3

This example demonstrates the deposition performance of polystyrene latex particles on virgin hair and tip hair.

3a) Preparation of Shampoo Base

The shampoo base was formulated by following standard process for shampoo. The shampoo base contained 12 wt % of sodium laurethsulfate, 1.60 wt % of cocamidopropyl betaine, 1 wt % of sodium chloride, and was balanced by water.

3b) Measurement of Deposition Ratio on Hair

Hair switches (virgin hair having length of 5.5 cm and weight of 750 mg, or tip hair having length of 5.5 cm and weight of 350 mg) were soaked into aqueous solution of 14 wt % of SLES at 40° C. with continuous shaking for 30 minutes. Then these hair switches were rinsed by tap water thoroughly and dried at ambient environment overnight.

Three hair switches were wetted with tap water and swung to remove excess water. The three hair switches were rubbed respectively with a mixture of 70 mg of shampoo base (or condition base) and 20 μl of 0.5 wt % of particles water dispersion of Table 4, and rinsed by 500 ml of tap water.

The switch was swung dry and then immersed in a vial containing 20 milliliters of ethyl acetate for 30 minutes. 200 microliters of the extraction liquid was withdrawn from the vial and added to a 96-well microplate for fluorescence measurement (excitation 441 nm, emission 500 nm) to afford a reading of $E_1$. The second switch was wetted with tap water and swung dry, to which 20 μl of the 0.5% of unmodified latex was added. The switch was also extracted with 20 milliliters of ethyl acetate for 30 minutes. 200 microliters of the extraction liquid was withdrawn and added to the microplate and subjected to measurement using the aformentioned method and afforded a reading of $E_0$. The third switch was extracted without added any latex in 20 milliliters of ethyl acetate for 30 minutes. 200 microliters of the extraction liquid was taken to the microplate and afforded a reading $E_b$ upon fluorescence measurement.

The percent deposition (% deposition) was calculated according to the following equation:

$$\% \text{ Deposition} = \frac{E_1 - E_b}{E_0 - E_b} \times 100.$$

Table 4 shows the deposition results on virgin and tip hair via incorporating the particles into shampoo base. The averages and standard derivations are calculated from 5 tests.

TABLE 4

Deposition performance

| Code of latex particles | Deposition on virgin hair (%) | Deposition on tip hair (%) |
|---|---|---|
| PS | 3 ± 1 | 4 ± 1 |
| PS-graft-Chitosan-P1 | 17 ± 2 | 26 ± 2 |
| PS-graft-Chitosan-P5 | 36 ± 4 | 23 ± 9 |
| PS-graft-Chitosan-BMS | 23 ± 2 | 23 ± 6 |
| PS-graft-Chitosan-Phe | 16 ± 4 | 23 ± 5 |
| PS-graft-Chitosan-Ser | 15 ± 4 | 11 ± 1 |
| PS-graft-Chitosan-Pro | 9 ± 4 | 12 ± 1 |
| PS-graft-Chitosan-Arg | 13 ± 2 | 14 ± 2 |

As can be seen from Table 4, when incorporated into shampoo base, the particles PS-graft-Chitosan-P1, PS-graff- Chitosan-P5, PS-graff-Chitosan-BMS, and PS-graft-Chitosan-Phe had higher deposition ratio tip hair than PS-graff-Chitosan-Arg. The particles PS-graft-Chitosan-P1 and PS-graff-Chitosan-Phe had higher deposition ratio on tip hair than virgin hair.

The invention claimed is:

1. A benefit agent delivery particle comprising:
   a) a core comprising a benefit agent, wherein the benefit agent is selected from the group consisting of a fragrance, pro-fragrance, or mixture thereof;
   b) an inner shell comprising a water insoluble non-polysaccharide polymer, a water insoluble inorganic salt, or a mixture thereof; and
   c) an outer shell comprising a chitosan salt at the outer surface of the particle, wherein the chitosan salt comprises a chitosan component and one or more amino acid anions, wherein the amino acid comprises phenylalanine, the amino acid does not comprises tyrosine, and if the amino acid comprises histidine, it is not present in an amount greater than 20% by mole % of the total amino acid.

2. The particle according to claim 1 wherein the chitosan component of the salt has a viscosity average molecular weight of at least 10,000.

3. The particle according to claim 1 wherein the amino acid further comprises glutamine, glutamic acid, histidine, leucine, lysine, serine, threonine, or a mixture thereof.

4. The particle according to claim 1 wherein the amino acid is only phenylalanine.

5. The particle according to claim 1 wherein the benefit agent is only a fragrance.

6. The particle according to claim 1 wherein the water insoluble non-polysaccharide polymer is selected from the group consisting of polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccharide or a mixture thereof.

7. The particle according to claim 1 wherein the particle has an average particle size of 0.5 to 20 µm.

8. The particle according to claim 1 wherein at least 50% of the outer shell by weight is the chitosan salt.

9. A composition comprising:
   a) a particle of claim 1, and
   b) at least one surfactant.

10. A hair treatment composition comprising the particle of claim 1.

11. A process for the production of particle of claim 1, the process comprising:
    a) encapsulating a core using emulsion polymerization to form a particle, and
    b) attaching chitosan salt onto the outer surface of the particle,
wherein the benefit agent is either present in or as the core during step (a) of the process or adsorbed into the core in a subsequent step.

* * * * *